(12) United States Patent
Carmignani et al.

(10) Patent No.: US 6,902,653 B2
(45) Date of Patent: *Jun. 7, 2005

(54) APPARATUS AND METHOD FOR PHOTOCATALYTIC PURIFICATION AND DISINFECTION OF FLUIDS

(75) Inventors: Gary Carmignani, Occidental, CA (US); Lee Frederick, Santa Rosa, CA (US); Steve Sitkiewitz, Sebastopol, CA (US)

(73) Assignee: Titan Technologies, Sebastopol, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/294,909

(22) Filed: Nov. 15, 2002

(65) Prior Publication Data

US 2003/0150707 A1 Aug. 14, 2003

Related U.S. Application Data

(63) Continuation-in-part of application No. 09/721,803, filed on Nov. 22, 2000, now Pat. No. 6,524,447.
(60) Provisional application No. 60/166,855, filed on Nov. 22, 1999.

(51) Int. Cl.[7] .............................. C07C 6/00; C02F 1/48; B01J 19/08
(52) U.S. Cl. ................... 204/157.15; 210/748; 422/186; 422/186.3
(58) Field of Search .............................. 422/186, 186.3; 204/157.15; 210/748

(56) References Cited

U.S. PATENT DOCUMENTS

| | | | |
|---|---|---|---|
| 4,863,608 A | 9/1989 | Kawai et al. | 210/638 |
| 4,966,759 A | 10/1990 | Robertson et al. | 422/186 |
| 5,069,885 A | 12/1991 | Ritchie | 422/186 |
| 5,126,111 A | 6/1992 | Al-Ekabi et al. | 422/186.3 |
| 5,256,616 A | 10/1993 | Heller et al. | 502/350 |
| 5,302,356 A | 4/1994 | Shadman et al. | 422/186.3 |
| 5,308,454 A | 5/1994 | Anderson | 204/59 R |
| 5,395,522 A | 3/1995 | Melanson et al. | 210/202 |
| 5,501,801 A | * 3/1996 | Zhang et al. | 210/748 |
| 5,637,231 A | 6/1997 | Hill et al. | 210/748 |
| 5,736,055 A | 4/1998 | Cooper | 210/748 |
| 5,766,455 A | 6/1998 | Berman et al. | 210/199 |
| 5,790,934 A | 8/1998 | Say et al. | 422/186 |
| 5,866,752 A | * 2/1999 | Goozner | 588/227 |
| 5,868,924 A | 2/1999 | Nachtman et al. | 210/85 |

(Continued)

OTHER PUBLICATIONS

Suvorov, et al., "Oxidation of Organic Compounds, C. Vanndium Pentoxide–Titanium Catalyst for Oxidation and Oxidative Ammonolysis of Organic Compounds" Vesta. Akad. Nauk. Kaz., vol. 10, pp. 16–23, (no month available), 1974.

Primary Examiner—Edna Wong
(74) Attorney, Agent, or Firm—W. Jackson Matney, Jr.

(57) ABSTRACT

An apparatus and method for the photocatalytic conversion of contaminants in a fluid stream. Fluid is directed through a semitransparent packed bed or an open cell, three dimensionally reticulated, fluid permeable, semiconductor unit. Within the unit, a semiconductor, when exposed to a photoactivating light source, converts the contaminants through a photocatalytic reaction. Both the substrate and the semiconductor photocatalyst are semitransparent to the activating light to allow penetration of light into the unit, thereby distributing the light, increasing the active specific surface area, and improving the net conversion performance of the unit.

36 Claims, 7 Drawing Sheets

U.S. PATENT DOCUMENTS

| | | |
|---|---|---|
| 5,919,422 A | 7/1999 | Yamanaka et al. ............ 422/121 |
| 6,030,526 A | 2/2000 | Porter ..................... 210/198.1 |
| 6,054,227 A | 4/2000 | Greenberg et al. ........... 428/701 |
| 6,066,359 A | 5/2000 | Yao et al. ................. 427/126.3 |
| 6,117,337 A | 9/2000 | Gonzalez-Martin et al. 210/748 |
| 6,135,838 A | 10/2000 | Wang .......................... 445/22 |
| 6,136,186 A | 10/2000 | Gonzalez-Martin et al. ...................... 210/198.1 |
| 6,241,856 B1 | 6/2001 | Newman et al. .......... 204/157.3 |
| 6,306,796 B1 | 10/2001 | Suzue et al. ................. 502/350 |
| 6,340,711 B1 | 1/2002 | Ohmori et al. ................ 516/79 |
| 6,524,447 B1 * | 2/2003 | Carmignani et al. ...... 204/158.2 |
| 2001/0003358 A1 | 6/2001 | Terase et al. .................. 252/62 |
| 2002/0006866 A1 | 1/2002 | Ohmori et al. .............. 502/350 |
| 2002/0023800 A1 | 2/2002 | Ohmuri et al. .............. 181/294 |

* cited by examiner

APPARATUS AND METHOD FOR PHOTOCATALYTIC PURIFICATION AND DISINFECTION OF FLUIDS

This application is a continuation-in-part of U.S. patent application Ser. No. 09/721,803, which was filed on Nov. 22, 2000, now U.S. Pat. No. 6,524,447, and which claims priority from U.S. Provisional Application Ser. No. 60/166,855, which was filed on Nov. 22, 1999.

FIELD OF THE INVENTION

The present invention generally relates to a method and apparatus for the purification and disinfection of fluids. More specifically, the present invention relates to an apparatus and method of use of a semitransparent semiconductor material for the photocatalytic conversion of contaminants in fluids. The present invention discloses an apparatus and method incorporating a packed bed or rigid, open cell, three dimensionally reticulated, fluid permeable, photocatalytic semiconductor unit that is partially transparent to ultraviolet radiation.

BACKGROUND OF THE INVENTION

Heterogeneous photocatalysis is the general term that describes the technical approach. Mills, A., Le Hunte, S., "An Overview of Semiconductor Photocatalysis," J. Photo-Chem. & PhotoBio. A: Chemistry 108 (1997) 1–35; and Hoffman, M. R., Martin, S. T., Choi, W., Bahnemann, D. W., "Environmental Applications of Semiconductor Photocatalysis," Chem Rev 1995, 95, 69–96. Of particular importance is the formation of OH., the hydroxyl radical. The hydroxyl radical is an extremely potent oxidizing agent (redox potential of +2.8 eV vs. SHE (Standard Hydrogen Electrode)) that is capable of oxidizing almost all organic compounds. By comparison, the redox potentials for the more conventional oxidants chlorine and ozone are +1.36 and +2.07 eV, respectively. Hydroxyl radicals also kill and breakdown microorganisms and endotoxins.

Contaminants in fluid streams, such as organic compounds, nitrogen and sulfur oxides, acid gasses, dissolved inorganic solids, and microorganisms are converted by the oxidizing and reducing potential of the activated semiconductor. The conversion may take the form of, but is not limited to, the oxidation of organic compounds, degradation of microorganisms, or reduction of dissolved ionic species. The products of the conversion are ideally less harmful or more easily removed from the fluid stream than the parent compounds.

Semiconductor photocatalysts that have been demonstrated for the destruction of organic contaminants in fluid media include but are not limited to: $TiO_2$, $ZrO_2$, ZnO, $CaTiO_3$, $SnO_2$, $MoO_3$, $Fe_2O_3$, and $WO_3$. $TiO_2$ is the most widely investigated because it is chemically stable, has a suitable bandgap structure for UV/Visible photoactivation, and is relatively inexpensive.

$TiO_2$ exists as three principal crystalline forms: rutile, brookite, and anatase. The rutile form of $TiO_2$ is widely used as a pigment and can be found in almost anything white, e.g., paint, paper, textiles, inks, plastics and cosmetics. Anatase, the low temperature form, is the most photoactive form. One method for making a brookite-containing $TiO_2$ photocatalyst is described in U.S. Pat. No. 6,337,301, the disclosure of which is incorporated by reference in its entirety.

The inclusion of co-catalysts (e.g., platinum, palladium, silver and/or their oxides and sulfides) with titanium dioxide can increase the photocatalytic activity. A variety of methods improve the quantum efficiency of $TiO_2$ by adding various metals to increase the minority carrier diffusion length, Augustynski, J.; Hinden, J. Stalder, C.; J. Electrochem. Soc. 1977, 124, 1063, or achieve efficient charge separation to increase carrier lifetimes. Vogel, R., Hoyer, P., Weller, H., "Quantum-Sized PbS, CdS, Ag2S, Sb2S3 and Bi2S3 Particles as Sensitizers for Various Nanoporous Wide-Bandgap Semiconductors," J. Phys. Chem. 1994, 98, 3181–3188.

The inventors have found that the performance of a photocatalytic fluid purification device is primarily a function of the activity of the semiconductor photocatalyst, the specific surface area of the irradiated semiconductor surface, the mass transfer characteristics of the device, the pressure drop across the device, and light distribution and absolute light intensity at the semiconductor surfaces. All of these factors should be considered concurrently in the design of the photoreactor. To take advantage of the activity of the semiconductor surface, conditions are preferably controlled such that the rate of transport of contaminants from the fluid bulk to the semiconductor surface is not a limiting factor. Because the rate of contaminant conversion increases with increased surface concentration of the contaminant, the concentration gradient between the fluid bulk and the fluid at the semiconductor surface should be preferably minimized. The mass transfer characteristics of the device increase with the velocity of the fluid through the device and with closer proximity of the bulk fluid to the semiconductor surfaces. Preferred mass transfer characteristics are achieved by altering pore diameter, packing diameter, or otherwise physically ensuring small characteristic lengths. Forcing the fluid to flow in a tortuous path past the semiconductor surfaces also inherently improves mass transfer.

According to the invention, the absolute conversion rate is a function of the surface concentration of the organic compound, the light intensity, and the irradiated surface area. The inventors believe that the reaction order in light intensity is <1, and that it is half order based on theoretical consideration of the accepted reaction mechanism and observed experimentally. Gerischer, H., *Electrochimica Acta* 38, 9 (1993) and Turchi, C. S., Ollis, D. F., *Journal of Catalysis* 119, 483 (1989). Based on the inventors' understanding that the reaction order for light intensity is less than unity, it is desirable to spread the light from a given source over as much surface area as possible. Therefore, according to the principles of the invention, an efficient device is one that provides intimate contact between the fluid and the semiconductor surfaces while spreading activating light over as large a surface area as is practical. Note that if the reaction order were, in fact, unity in light intensity, increasing the specific irradiated surface area, for a given light source, would not improve performance.

Since until recently known semiconductor surfaces have been opaque to UV light; the spreading of light has typically been done by using geometry or waveguides. U.S. Pat. No. 5,516,492, to Dong, uses a plurality of curved plates while U.S. Pat. No. 6,063,343, to Say, uses a series of close packed plates orientated normal to the lamp axis to provide high specific irradiated surface area. U.S. Pat. No. 6,285,816, to Anderson, uses a waveguide to distribute the light. The previously mentioned methods rely on geometry or optics to distribute light to a semiconductor film and do not rely on a semitransparent substrate/semiconductor film pairing for radiation distribution.

Much of the early research on semiconductor photocatalysis concerned methods using opaque titanium dioxide ($TiO_2$) slurries or $TiO_2$ wash coatings onto or inside a glass tube and the photodegradation of organic compounds and their intermediates in water. These methods of using $TiO_2$ have limitations for commercial applications. For example, $TiO_2$ slurry has the serious limitation of the removal of the $TiO_2$ particles from the purified water. While wash coating $TiO_2$ onto glass avoids the removal limitations of the slurry approach, it has its own problems in that insufficient surface area is presented for effective destruction of organics within a reasonable time period. Additionally, the wash coat is not firmly attached to the glass resulting in a loss of $TiO_2$ to the water stream and a concomitant reduction in photocatalytic activity.

Kraeutler and Bard made a photocatalytic reactor with a water slurry of suspended $TiO_2$ powder, in the anatase crystalline form, and studied the decomposition of saturated carboxylic acid. J. ACS 100 (1978) 5985–5992. Other researchers used UV-illuminated slurries of $TiO_2$ to study the photocatalyzed degradation of organic pollutants in water.

Mathews created a thin film reactor by wash coating $TiO_2$, (Degussa P25™), particles to the inside of a 7 millimeter long borosilicate glass tube wound into a 65-turn spiral. He monitored the destruction of salicylic acid, phenol, 2-chlorophenol, 4-chlorophenol, benzoic acid, 2-naphthol, naphthalene, and florescin in water. J. Physical Chemistry 91 (1987) 3328–3333. U.S. Pat. No. 5,766,455, to Berman, wash coated an opaque coating onto a glass fiber mesh. Neither of these devices uses a transparent substrate/semiconductor pairing.

U.S. Pat. No. 4,892,712, to Robertson et al., discloses the attachment by the sol-gel process of anatase $TiO_2$ to a fiberglass mesh substrate. This mesh was wrapped around a light source contained within a quartz glass cylinder and emitting UV radiation in a wavelength range of 340 to 350 nanometers (nm). Unlike the present invention, Robertson's mesh is not rigid, lacks permanent bonding of the semiconductor to the mesh, and does not specify the transparency of the substrate semiconductor pairing.

Professor I. R. Bellobono prepared photocatalytic membranes immobilizing 23% of Titanium Dioxide (Degussa P-25). Controlled amounts of appropriate monomers and polymers, containing the semiconductor to be immobilized and photoinitiated by a proprietary photocatalytic system was photografted onto a non-woven polyester tissue. The final porosity of the photosynthesized membrane was regulated at 2.5–4.0 microns. He trade named this membrane "Photoperm"™. "Effective Membrane Processes. New Perspectives," R. Paterson, ed., BHR, Mech. Eng. Publ., London (1993), 257–274. The process was patented in Italy in 1995, Italian Pat. No. IT1252586. Unlike the present invention, Bellobono's apparatus is not inert, not durable, and would display excess pressure drop due to low fluid permeability.

Cittenden, et al. discloses a method and apparatus for destroying organic compounds in fluids. See The 1995 American Society of Mechanical Engineers (ASME) International Solar Energy Conference, Maui, Hi., USA. An opaque coating of $TiO_2$ was attached by wash coating to a 35×60-mesh silica gel substrate. The substrate was placed within a plastic tube that allowed the penetration of UV light. Organic pollutants in a water stream passed axially through the tube. Unlike the present invention with a semi-transparent semiconductor coating, Cittenden's invention is not durable, the photocatalytic coating is not semitransparent, and has very limited fluid permeability.

Another method to make ceramic titanium membranes uses a refined sol-gel process. J. Membrane Science 30 (1988) 243–258, and U.S. Pat. No. 5,006,248, to Anderson. These membranes are porous and transparent to UV illumination. They are made from a titanium alkoxide and then fired to form the anatase crystalline structure. Unlike the present invention, Anderson's invention has very limited fluid permeability.

Thus, while attempts have been made in the prior art to enhance quantum yields by increasing semiconductor specific irradiated surface area and improving UV light penetration, serious limitations remain to the commercial development of an efficient, durable, photocatalytic purification apparatus with acceptable pressure drop characteristics and methods for its use.

SUMMARY OF THE INVENTION

The object of the present invention is to substantially improve upon the prior art to produce an effective, efficient, durable, economic, commercial apparatus for the rapid photocatalytic purification and disinfection of fluids. One embodiment of the invention is a reactor that includes a semitransparent packing material, a semitransparent semiconductor coating supported on the packing, and one or more light sources. The light sources are situated within the packed bed so that light may be transmitted through multiple semiconductor coating layers. The fluid is purified as it flows through the packed bed.

The effectiveness of the process is determined in part by the mass transfer efficiency, which is the rate at which the contaminant is transported from the fluid stream to the photocatalytic surface where it may be destroyed. The embodiment consisting of a semitransparent packing/semiconductor pairing provides for high specific surface area and adequate contacting of the surfaces with the treated fluid. The characteristic length associated with the substrate (packing) is kept as small as practical, within the constraint placed by allowable fluid pressure drop across the device.

Another consideration is the distribution of light to the semiconductor surfaces within the device. Since the semiconductor coating is semitransparent to the activating light, a portion of the photons are absorbed by the photocatalyst coated on the substrate, or within the substrate, and the remainder are passed onto an adjacent photocatalytic surface. Thus, the volume fraction of support material should be minimized and it should have high transparency to the activating photons. To enhance volumetric illumination, in an embodiment that employs a substrate, the substrate material is preferably made from glass or other materials transparent or semitransparent to the photoactivating wavelengths. The semiconductor coatings should also display high transmission of light to provide for a large irradiated surface area. In an embodiment which bonds or chemically integrates the substrate with the semiconductor, the unit is also preferably made from transparent or semitransparent materials.

The transparent/semitransparent reticulated or packed bed semiconductor unit utilized in the present invention substantially represents a breakthrough over the prior art and allows for the commercial use of photocatalytic technology in fluid purification because it optimizes device performance by balancing consideration of mass transfer, irradiated surface area, radiation distribution, and pressure drop while providing durability and ease of device manufacture and maintenance. The photocatalytic semiconductor unit provides a high surface area, transparent structure to which a semi-transparent semiconductor photocatalyst is adhered or incorporated.

DETAILED DESCRIPTION OF PREFERRED EMBODIMENT

The present invention is directed to the use of a semiconductor unit that consists of a photocatalyst coated packed bed or three dimensionally reticulated, semitransparent, permeable semiconductor unit for use in a reactor apparatus and method for the purification and disinfection of fluids. The invention may be used, for example, in the semiconductor and pharmaceutical industries, for environmental cleanup, for the home point-of-use market, and for air purification. One familiar with the art recognizes that the current invention may be used to purify fluids in many different industries and applications.

In a preferred embodiment, the present invention discloses an apparatus and method for purifying fluids, principally air and water, that solves problems of the prior art by presenting a fluid to a packed bed or a rigid, three dimensionally reticulated, open-cell material characterized by an inert, fluid permeable, high surface area semitransparent substrate onto which a semitransparent photocatalytic semiconductor layer is permanently bonded or into which it is incorporated. The material described in the present invention and the apparatus and method for its use in photocatalytic purification and disinfection of fluids is further characterized by high mass transfer efficiency with relatively low pressure drop.

Figure 1:
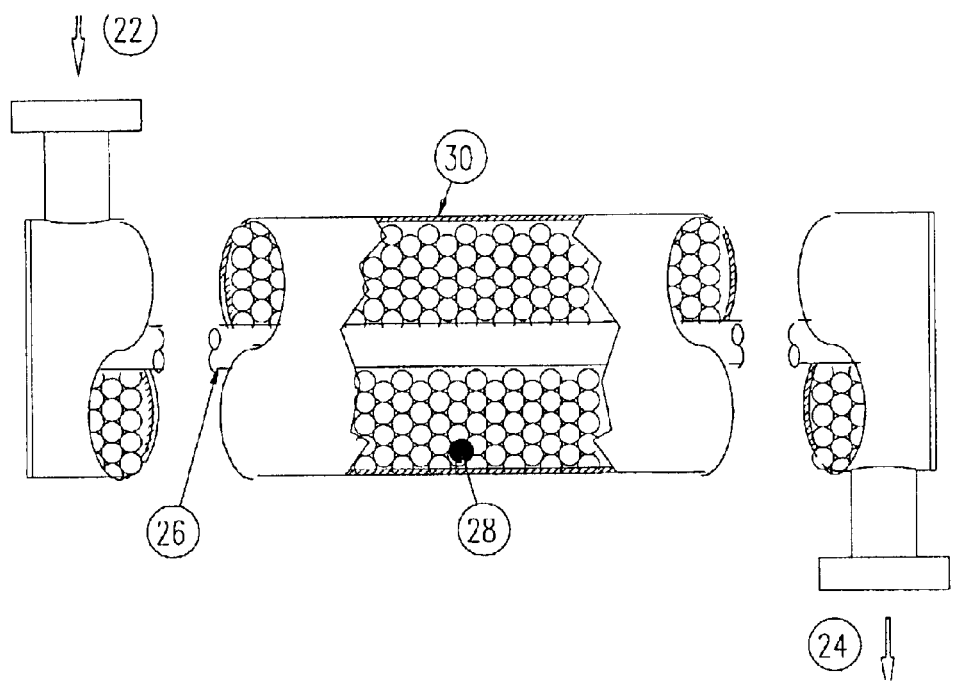
FIG. 1 shows a packed bed annular reactor.

One embodiment of the invention is illustrated in FIG. 1. A reactor is composed of a cylindrical chamber 30 with one or more fluid inlet ports 22 and one or more fluid outlet ports 24. The chamber 30 is constructed of a material resistant to corrosive effects of the fluid, for example stainless steel alloys for water applications or aluminum alloys or plastic for air applications. The inlet and outlet ports 22, 24 are configured to provide for flow axially through the reactor. A lamp sleeve 26, transparent to the radiation wavelength of interest, is situated parallel to the axis of flow in the center of the chamber. A bed of semitransparent semiconductor coated semitransparent packing material 28 is situated in the annulus between the wall of the chamber 30 and the lamp sleeve 26. The required light source (not shown) is centered within the sleeve.

According to the invention, the radius of the chamber is chosen to control the fraction of the light entering the semiconductor unit at the lamp sleeve that passes through the unit unabsorbed. The ratio of the light flux at the chamber wall to the light flux at the lamp sleeve is preferably 0.001–0.2 and more preferably 0.05–0.10. For a given ratio the radius is determined by the size of the packing material and the transparency of the semiconductor coating. The size, shape, and type of packing are chosen to balance mass transfer, pressure drop, and cost considerations. Packing with smaller characteristic lengths will result in improved mass transfer and lower device weight but will result in larger pressure drop. Some packing material types have higher specific surface area than others, but the cost of the more complicated of these may be prohibitive. The light source is chosen to provide the wavelength appropriate for the particular semiconductor in use considering activation and transparency factors. Light sources with higher linear energy density are preferred, however, lamp cost and efficiency (relating to power cost) are also considerations.

Figure 2:
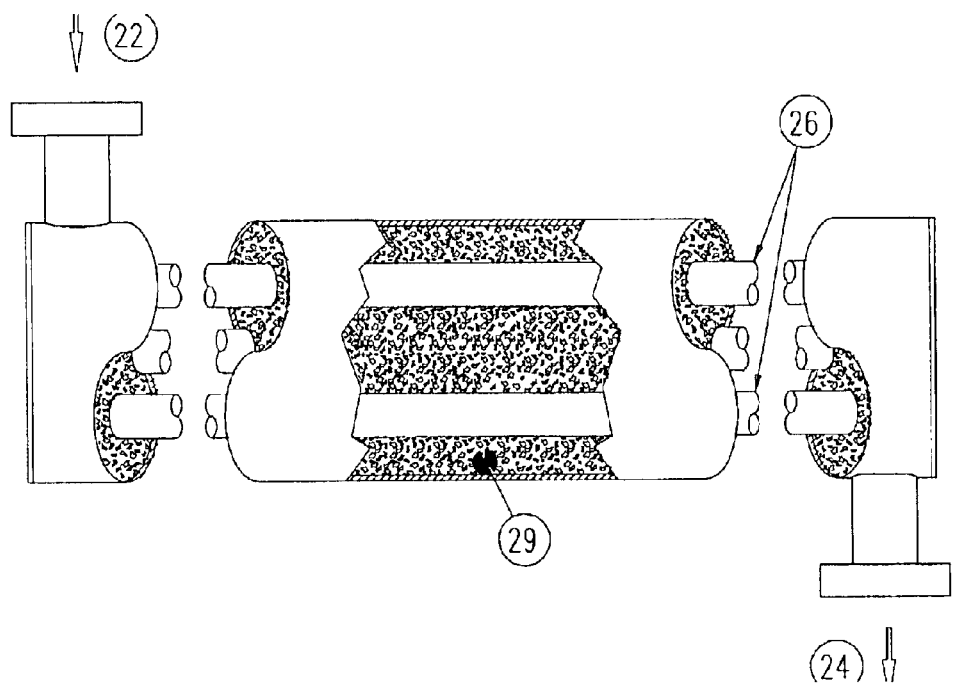
FIG. 2 shows an annular reactor with a reticulate foam substrate and multiple lamps.

Another embodiment of the invention is illustrated in FIG. 2. This embodiment is similar to that described by FIG. 1, except that the substrate is a semiconductor coated reticulated structure 29 such as a reticulated foam or a structure fabricated using stereolithography and multiple light sources (not shown) are used in the device. More light sources simply allow a larger fluid throughput for each reactor.

Figure 3:
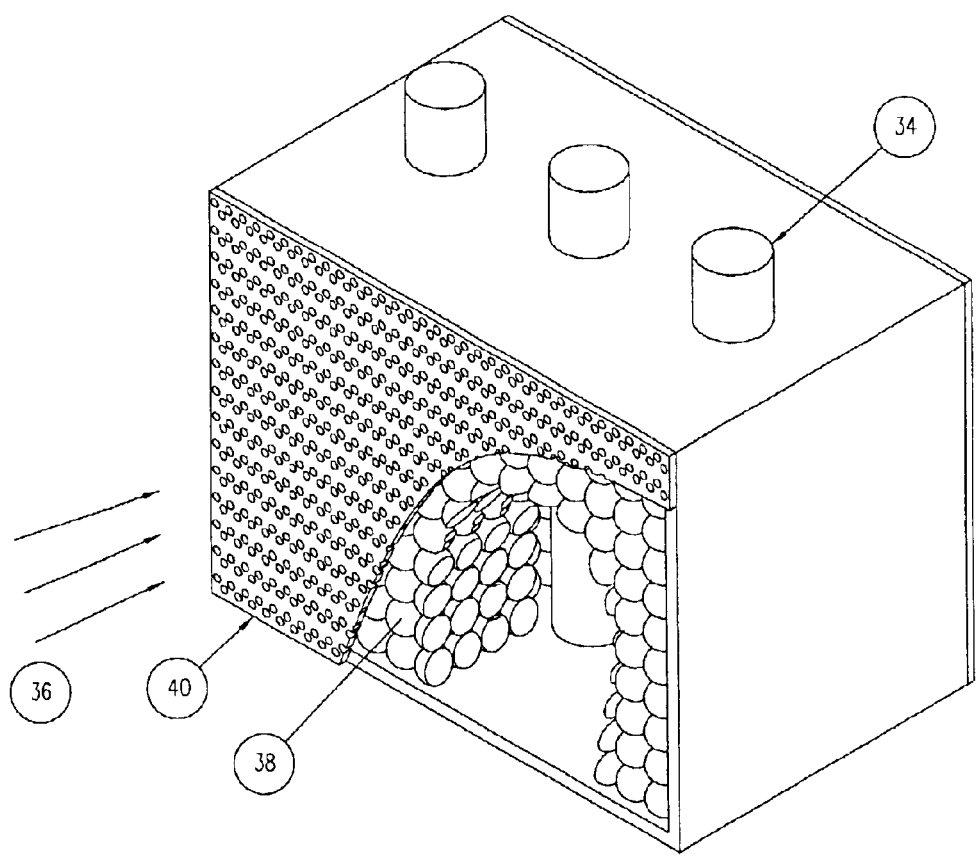
FIG. 3 shows a packed bed in a rectangular configuration with multiple lamps.

Another embodiment of the invention is illustrated in FIG. 3. This embodiment uses a rectangular packed bed of semiconductor coated packing 38 supported by containment screen 40 with multiple lamps 34. Fluid flows 36 through the bed normal to the plane encompassing the lamps 34. The ratio of light intensity at the exit and entrance planes, and the outer walls of the housing to that at the lamp sleeves is preferably 0.001–0.2 and more preferably 0.05–0.1. The number of lamps used for a given reactor volume and throughput determines contaminant conversion performance; as more lamps are used, performance increases and the weight of the reactor may be lessened, but at the cost of increased power usage.

Figure 4:
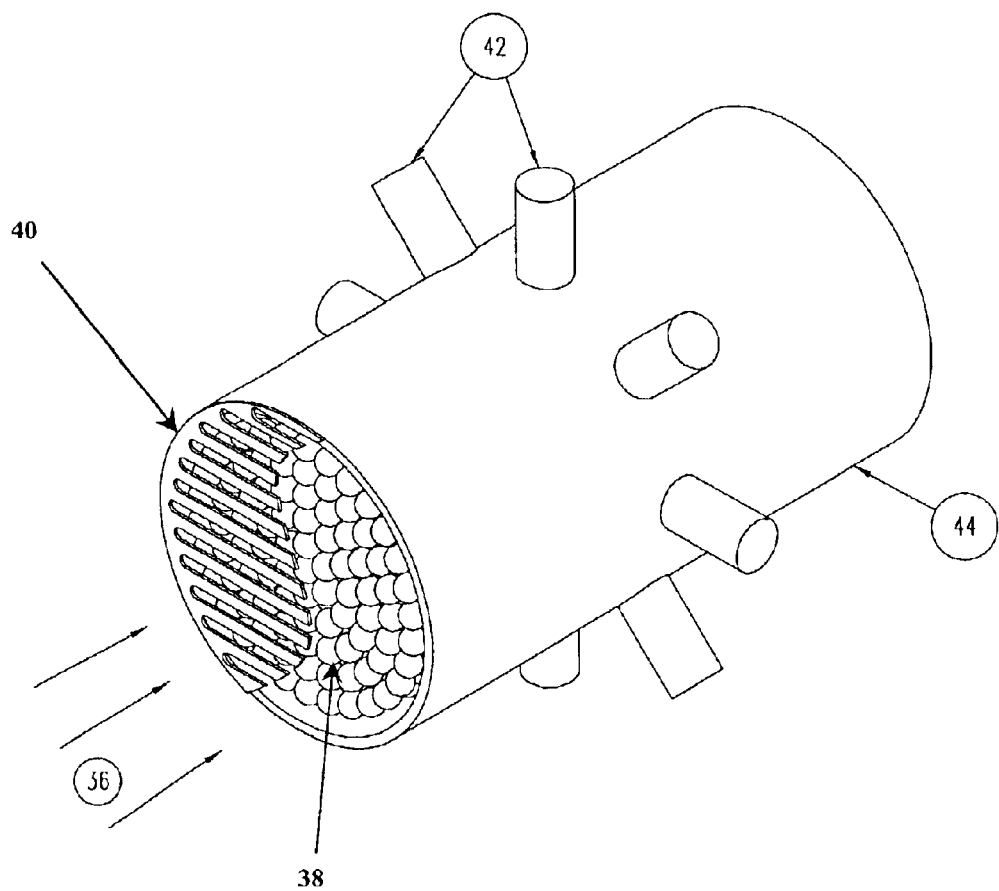
FIG. 4 shows a packed bed cylindrical reactor using LEDs as the light source.

Another embodiment of the invention is illustrated in FIG. 4. This embodiment uses a cylindrical packed bed of semiconductor coated packing 38 irradiated around the circumference with LEDs as the light source 42. A reticulated substrate could also, obviously, be used. The containing cylinder 44 is made from material resistant to fluid corrosion and degradation due to light emitted by the LEDs. The diameter of the housing is determined, in concert with the packing diameter and semiconductor coating light transmission, to give a ratio of light intensity at the center of the reactor to that at the outer radius of 0.001–0.2. This embodiment is ideal for applications with low throughput requirements or where extensive recycling of the fluid through the device is possible, for example in a device for treating potable water. The LEDs may prove superior to conventional lamps due to longer life, higher efficiency, lower thermal load, increased design flexibility, and lower voltage power requirements.

Figure 5:
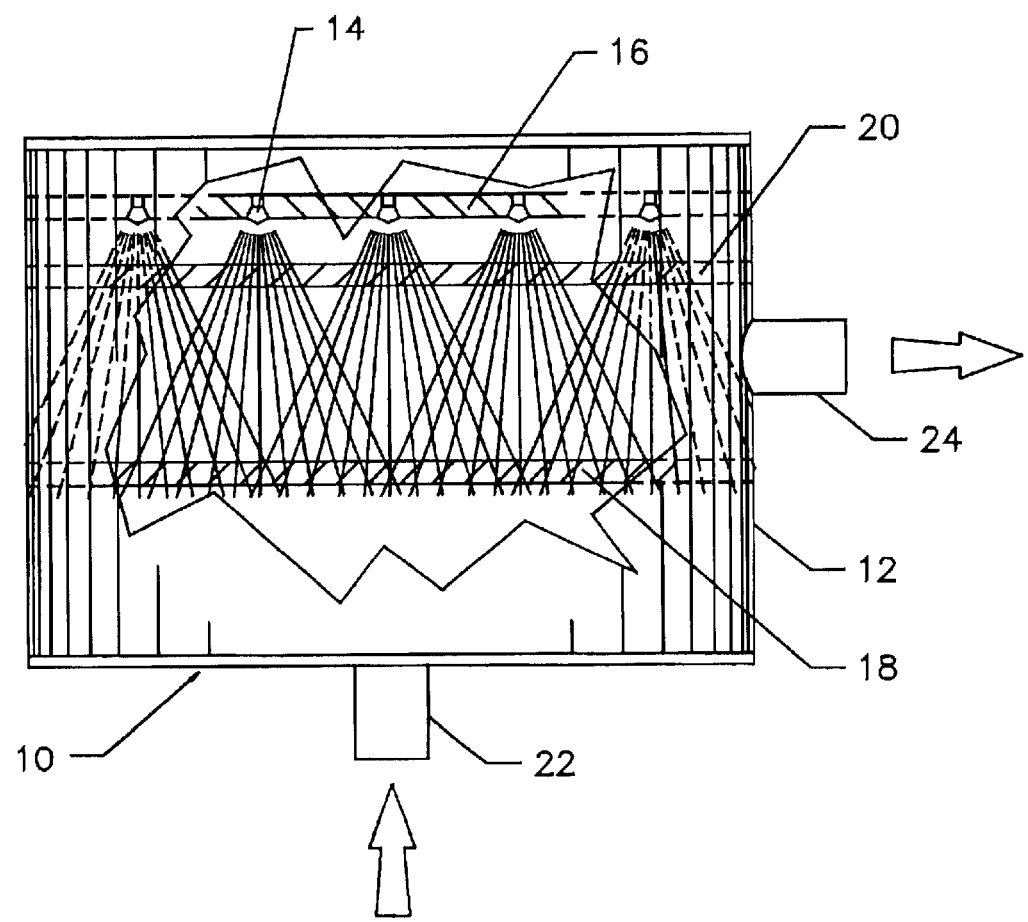
FIG. 5 shows another reactor using LEDs as the light source.

FIG. 5 shows an example of a point of use reactor 10 with LED's as the photoactivating light. Contaminated source water flows into the reactor through inlet 22. The water flows through the reticulated semiconductor unit 18 that is photoactivated by LED lights 14. A support/wiring plate 16 holds the LED lights. A quartz plate 20 is provided to isolate the LED lights from the water flow. Purified water exits the reactor through outlet 24. The point of use reactor enclosure 12 may be constructed from a variety of thermoplastics (polyproplylene, etc), or metals (304 stainless steel, 316 stainless steel, etc), or other materials that are both inert to degradation by the LED light source and resistant to corrosion by water.

The point of use reactor may use a reticulated or packed bed semiconductor unit that is photoactivated by LED's that emit UV energy at 370 nm or lower. The point of use reactor may also use a semiconductor unit that is doped to shift the band gap to visible wavelengths. In this example, an LED that emits visible wavelengths is utilized. This latter configuration enables a more efficient use of the LED energy.

The point of use reactor is designed to be commercialized into markets defined by low and intermittent demand for purified water, such as potable water in the home. This reactor is superior to existing technologies because it uses only a small percentage of energy and it does not transmit heat to the product water while not in use, which eliminates the need to rinse the system to ambient temperature prior to using product water. In addition, the reactor only requires low power electrical energy per LED, making it both safe for the user in an environment that includes water and electricity and enabling the reactor to be utilized in portable applications, such as battery powered option.

Although never before used for the present purpose, transparent packing materials and three dimensionally reticulated, open-cell substrates made from a variety of materials are scientifically described and commercially available. Such materials include alumina, zirconia, titania, silica, fused silica, glass, silicone, and organic polymers. In one preferred embodiment, substrate materials that are transparent or semitransparent to light and transmit greater than 80% of the light through a 1 cm thickness are used. The substrate is selected to give the required transparency to the activating light required by the semiconductor. For $TiO_2$ and light with a wavelength of 365±25 nm, substrates such as soda lime glass, borosilicate glass, or quartz may be employed. The substrate materials may take the form of packing materials and may be disposed in a column or other container. In a preferred embodiment, the substrate materials may be semitransparent random or regular or stacked packings, and may include spheres, cylinders, Raschig rings, Lessing rings, partition rings, Berl saddles, Intalox saddles, and various other saddle-shaped packings, Pall rings, Flexirings, Cascade rings, Hy-Pak rings, Tellerettes, various knitted or woven wire screen arrangements, or other materials in various arrangements or configurations that absorb <20%/cm of UV radiation at 365 nm±25 nm and have high specific surface area, structural integrity, and desirable fluid-flow characteristics. One of many methods of making a reticulated substrate is described in the prior art: U.S. Pat. Nos. 3,052,967, to Fischer; 3,946,039, to Walz; 4,568,595, to Morris; and 5,441,919, to Park et al. Substrates may also be made utilizing the stereolitograhic process or selective laser sintering or other methods familiar to those experienced in the art. The characteristic length and physical appearance of the substrate is chosen to maximize mass transfer characteristics while maintaining pressure drop below that acceptable for the given fluid, flow rate, and application. The characteristic length is preferably 0.05–2 cm, and more preferably 0.4–1 cm for packing materials and 0.1–0.5 cm for reticulate structures.

Many techniques are available to deposit the semiconductor on or within the substrate, including, without limitation, dip coating, sol-gel processing, chemical vapor deposition, aerosol application, evaporation deposition, inorganic binder attachment, organic/inorganic binder attachment. Literature and the prior art explain the procedures necessary for permanent bonding of semitransparent semiconductor layers to a substrate. See, for example, in patents, U.S. Pat. No. 6,337,301, to Ohmori, et al.; U.S. Pat. No. 6,013,372, to Hayakawa, et al., and U.S. Pat. No. 6,093,676, to Heller, et al.; and in literature, "Preparation, Microstructure and Photocatalytic Activity of Porous $TiO_2$ Anatase Coatings by Sol-Gel Processing," J Sol-Gel Science and Technology 17 (2000) 163–171, by Jiaguo Yu et al; "Nanocrystallite Titanium Dioxide Films Made by the Sol-Gel Method Using Reverse Micelles," J Sol-Gel Science and Technology 10 (1997) 83–89, by E. Stathaios, et al. For chemical vapor deposition refer to U.S. Pat. No. 5,389,401, to Gordon, and "Metal Organic CVD of Nanostructured Composite $TiO_2$—Pt Thin Films: A Kinetic Approach," Chem. Vapor Deposition 5 (1999) 13–20, by Giovanni et al. Yet another method condenses from aerosolized semiconductor droplets, as described in "Deposition of Multifunctional Titania Films by Aerosol Routes," J. Am. Ceramic Soc. 82 (1999) 10, by G. Yang and Pratim Biswas. While these are some of the popular methods for attaching semiconductor films, we do not limit ourselves to variations on them and other methods that are to be found in prior art.

In a further embodiment the substrate is made of the same material as the semiconductor layer and the two materials are chemically integrated.

Semiconductor photocatalysts suitable for use include but are not limited to $TiO_2$, $ZrO_2$, $ZnO$, $CaTiO_3$, $SnO_2$, $MoO_3$, $Fe_2O_3$, and $WO_3$. While various semitransparent semiconductor coatings may be employed, $TiO_2$ has provided effective results. In one preferred embodiment, the brookite form of $TiO_2$ along with a non-hydrolyzable zirconium compound was utilized as a coating material and provided effective results. Various other combinations of materials may be useful coating materials, such as mixtures of the polymorphs of $TiO_2$ alone or in combination with zirconium and/or tin oxides including, but not limited to, the following mixtures of brookite and anatase $TiO_2$; mixtures of brookite, anatase, and rutile $TiO_2$; mixtures of brookite $TiO_2$ and zirconium dioxide; mixtures of brookite and anatase $TiO_2$ and zirconium dioxide; mixtures of brookite, anatase, and rutile $TiO_2$ and zirconium dioxide; anatase $TiO_2$; mixtures of anatase $TiO_2$ and zirconium dioxide; mixtures of brookite $TiO_2$ and tin dioxide ($SnO_2$); mixtures of brookite and anatase $TiO_2$ and tin dioxide; mixtures of brookite, anatase, and rutile $TiO_2$ and tin dioxide; mixtures of anatase $TiO_2$ and tin dioxide; and rutile $TiO_2$. Co-catalysts, such as Pt, Ag, or Fe and the oxides and sulfides of these metals may be used to enhance conversion rates or shift the absorption spectra of the semiconductor. Other known semiconductors and co-catalysts may be used in this invention.

The activating light wavelengths differ among semiconductor photocatalysts. Light in the range of 200–400 nm UV is used in conjunction with $TiO_2$; the $TiO_2$ being partially transparent to UV of wavelengths 365±25 nm. For example, at longer wavelengths a semiconductor photocatalyst is more transparent, resulting in more efficient use of a given amount of light but requiring a larger reactor size. The specific wavelength for a given application is chosen to balance various considerations including power cost and reactor size/weight considerations. Both shorter or longer wavelengths may be used for a different semiconductor, or if the $TiO_2$ were modified in some way to change its absorption characteristics, say with a co-catalyst or a visible light activated dye. A preferred coating is semitransparent and transmits 60–95% of the light, preferably 70–90% of the light, and more preferably 75–85% of the light. Semiconductor coatings are preferably 0.1–1.0 $\mu$m thick.

Photocatalytic activity of many semiconductor surfaces is enhanced by adding a variety of co-catalysts, including transition metals such as, but not limited to, platinum, palladium, ruthenium, iridium, rhodium, gold, silver, copper, tin, iron, cobalt, vanadium, niobium, zirconium, and zinc. Combinations of these metals and their oxides, sulfides or other compounds are known to those experienced in these arts. Alternatively, the band gap energy of a semiconductor may be shifted to the visible spectrum (400 nm–700 nm) by adding co-catalysts or modifying the semiconductor surface with compounds such as light activating dyes. Zang et al. showed that the addition of platinum (IV) halide shifted the band gap energy required for $TiO_2$ from 366 nm to 400 nm into the visible spectrum. "Amorphous Microporous Titania Modified Platinum (IV) Chloride—A New Type of Hybrid Photocatalyst for Visible Light Detoxification," J Phys. Chem. B 102 (1998) 10765–10771. Doping with iron or chromium produces similar results. "Visible Light Induced Water Cleavage in Colloidal Solutions of Chromium-doped Titanium Dioxide Particles," J ACS 104 (1982) 2996–3002, by E. Borgarello et al. Other co-catalysts known to those with skill in the art may be used with this invention.

A further enhancement of the embodiments of the apparatus and method of the present invention consists of the use of a combination or set of substrate/semiconductor pairs each with its own particular variety of parameters and enhancements. Each member of the set may be designed to operate on a particular component of the TOC, such as, but not limited to, polar/non-polar components, hydrophobic/ hydrophilic components, aromatic/aliphatic components, alcoholic/acidic components and chemical/biological components. The members of the set are used in a series combination where water flows thru first one member and then another member. This enhancement enlarges the scope of the invention by bringing a complete collection of destruction capabilities to bear on combinations of contaminants, even though individual members of the set are alone incapable of acheiving acceptable overall TOC destruction levels.

The devices disclosed by this application may be interconnected in series or parallel to accommodate increased throughput or to give higher single pass conversion of contaminants.

The substrate for the devices disclosed by this application may be designed to allow removal so that the substrate/ semiconductor photocatalyst may be replaced with minimal effort.

A further enhancement of the devices disclosed by this application is to coat or polish the inner surface of the reactor chamber/housing to reflect residual light, not absorbed in the first pass through the multiple semiconductor coatings, back through the semiconductor unit.

A further enhancement of the devices disclosed by this application involves the addition of a distributor system on the inlet and/or outlet of the reactor to ensure uniform fluid flow distribution through the semiconductor unit.

Preferred light sources include, without limitation, low, medium and high-pressure mercury and xenon lamps and ultraviolet emitting LED's, or any other light source that activates the semiconductor, including sunlight.

Although particular embodiments of the present invention have been described and illustrated herein, it should be recognized that modifications and variations might readily occur to those skilled in the art and that such modifications and variations may be made without departing from the spirit and scope of our invention. Consequently, our invention as claimed may be practiced otherwise than as specifically described.

EXAMPLES

Example 1

$TiO2$ coatings were applied to three 1-inch samples of soda lime glass slides having a coating thickness of approximately 300–500 nm. For Sample 1, a semitransparent 100% anatase $TiO_2$ photocatalytic coating was applied using a standard sol gel method. Sitkiewitz, S. D., Heller, A., *New J. Chem* 20, 233–241 (1996). The semitransparent 100% anatase $TiO_2$ photocatalytic coating of Sample 2 was prepared using the refined sol gel method of Dr. Marc Anderson. U.S. Pat. No. 5,006,248. The photocatalytic coating of Sample 3 contained a mixture of brookite and anatase $TiO_2$ plus a zirconium compound having about 3 to 200 parts by weight $ZrO_2$ per 100 parts by weight of the metal oxide particles. The semitransparent coatings of Samples 1–3 had greater than 75% transparency to 365 nm radiation.

The photoactivity metric used to compare Samples 1–3 was the oxidation rate of salicylic acid. For each sample the slide was immersed in 20 ml of 10 ppm salicylic acid and irradiated with 254 nm light having an intensity of 575 $\mu W/cm2$. The oxygen concentration in the solution was maintained at saturation. The salicylic acid concentration was monitored as a function of time and the resulting data used to calculate a half-life for each test. The half-life is the time it takes to reduce the concentration of salicylic acid by half, assuming first order kinetics. The shorter the half-life the faster the salicylic acid was oxidized. Therefore, a shorter half-life demonstrates increased photocatalytic activity of the $TiO_2$ coating.

The photoactivity results for samples 1–3 are summarized below.

| Sample | Coating | Half-Life (min) |
|---|---|---|
| 1 | 100% anatase (standard sol gel) | 253 |
| 2 | 100% anatase (refined sol gel) | 168 |
| 3 | brookite and anatase $TiO_2$ plus $ZrO_2$ | 54 |

The half-life for Sample 3 (brookite/anatase mixture) was about five times shorter than the half-life for Sample 1 and about three times shorter that the half-life for Sample 2. As such, the photoactivity of the brookite/anatase coating was superior to that of the anatase coatings.

Example 2

Figure 6:
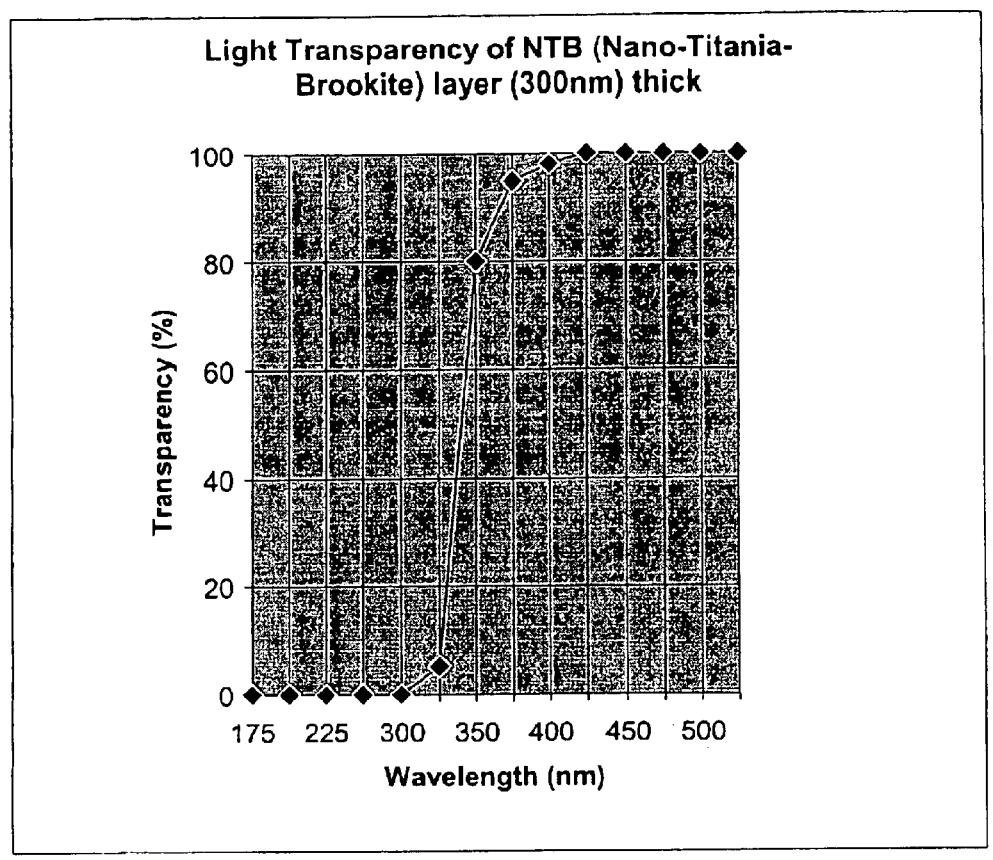
FIG. 6 shows the transmission curve for a semitransparent substrate/semiconductor pairing.

A semitransparent coating containing a zirconium oxide and brookite and anatase $TiO_2$ was applied to a quartz slide using dip coating process. As shown in FIG. 6, there is significant transmission of light around 365 nm, the emission wavelength of typical "blacklight" UV sources. As the photon energy is increased, a successively larger fraction of the incident energy is absorbed by the semiconductor coating. For the current invention the rate of oxidation of organic compounds, under typical operating conditions, can be expressed as:

$$\text{rate} = kA((1-T)I)^n \Theta_{organic} [\text{moles or mass/time}] \quad (1)$$

where:

k=rate constant;

A=irradiated surface area;

T=fractional transmission of incident light through the photocatalytic layer;

I=incident light intensity;

Θ=surface concentration of organic compound; and, n=reaction order in light intensity—typically about 0.5. For typical opaque photocatalytic coatings T is essentially zero and the reaction rate is simply proportional to $I^{0.5}$.

Figure 7:
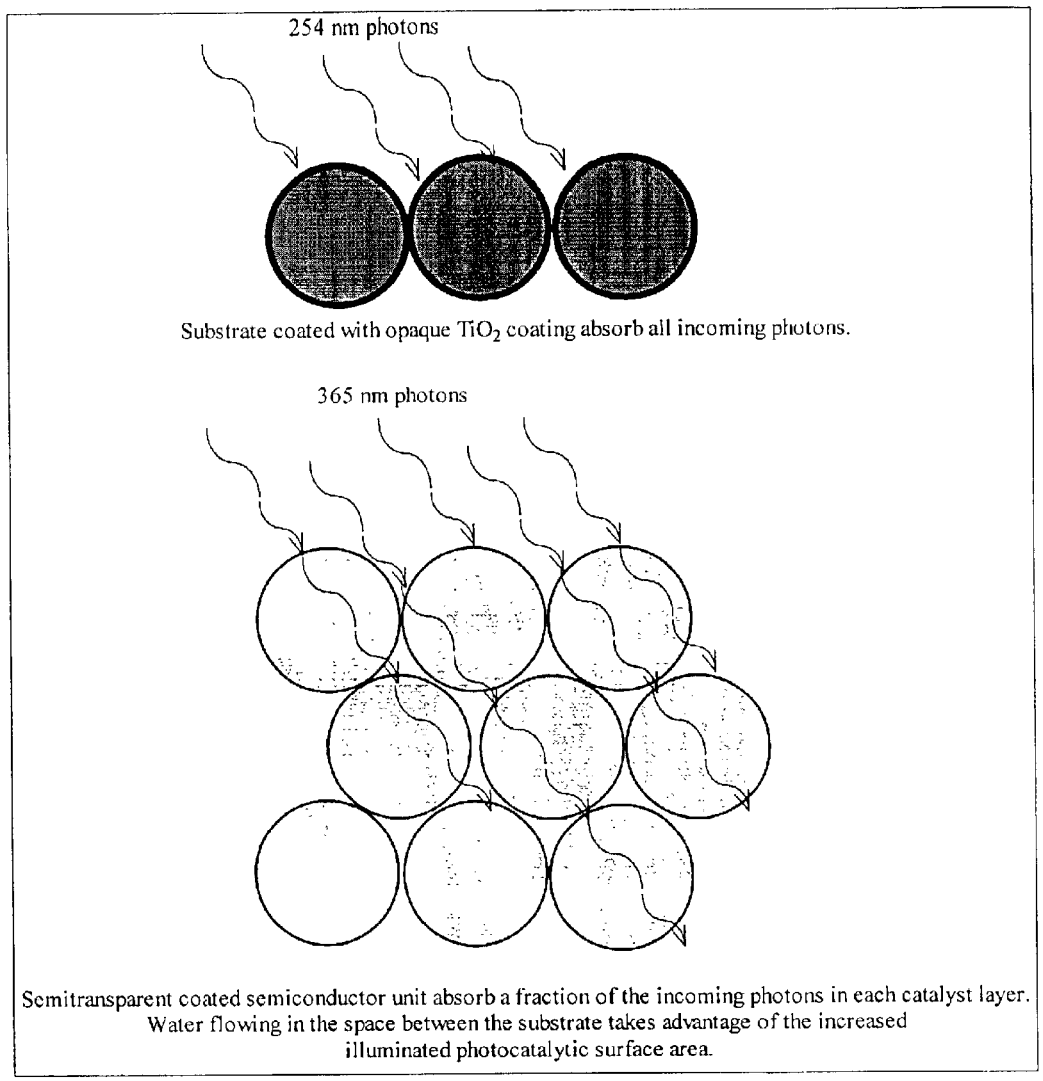
FIG. 7 illustrates the difference between opaque and semitransparent pairings.

Standard U sources have strong emissions at 254, 310, and 365 nm. For typical opaque film, where all of the incident light at both 254 and 365 nm is absorbed by the film, the 254 nm wavelength is preferred since it is desirable to localize the photon absorption as close to the film-fluid interface as possible as photons absorbed deep in the film, relatively far from the fluid, will not contribute to the oxidation of organic compounds. By using the information from FIG. 6 in conjunction with Equation 1 it is clear that an increased rate of reaction will be realized if thin films of $TiO_2$, irradiated at 365 nm, are used instead. Since the rate of reaction is less than unity with respect to light intensity, spreading the photons out over a larger area, as illustrated in FIG. 7, will give an increased rate of reaction for a given incident photon flux.

Figure 8:
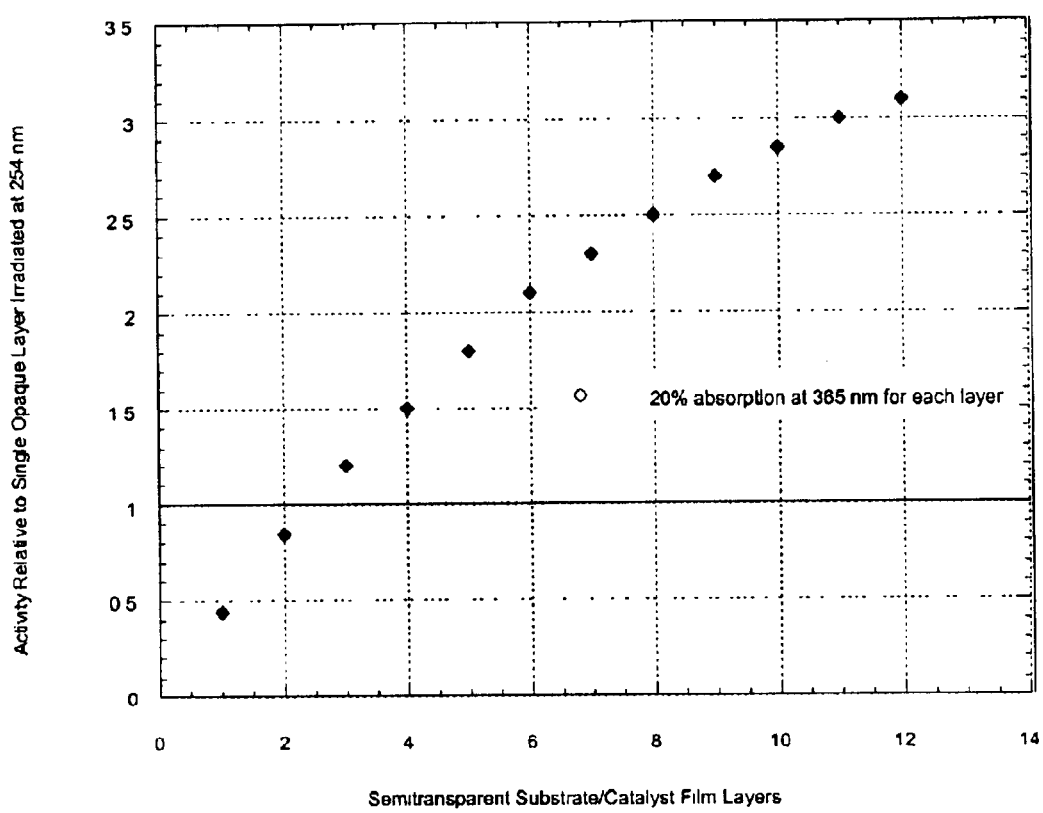
FIG. 8 shows the effect of the reaction rate being half-order in light intensity on system performance (quantum efficiency) for a semitransparent substrate/semiconductor pairing relative to an opaque system.

A comparison was made between a system using 254 nm light and an opaque film and one using 365 nm radiation and layers of semitransparent catalyst and substrate. For the same photon flux in both systems, the ratio of the rate of reaction of the 365 nm system relative to the 254 nm system can be expressed as:

$$\text{relative rate} = (1-T)^{0.5} \sum_{i=0}^{\#layers} T^{\left(\frac{i}{2}\right)} \quad (2)$$

where the number of layers is the number of individual catalyst coated surfaces penetrated. As shown in FIG. 8, for a catalyst film that absorbs 20% of the incident 365 nm light a system that uses more than three catalyst films will give a larger reaction rate than a single opaque coating.

Example 3

Semiconductor photocatalyst coated glass spheres were made and tested. Brookite and anatase $TiO_2$ plus $ZrO_2$ was coated onto 6 mm soda-lime glass spheres. The transparency of each coating layer to 365 nm light was about 85%. A packed bed of these spheres were placed in a test cell of radius 2.2 cm. Air at 40% relative humidity was passed through the bed at a flow rate of 40 $cm^3$/s. Formaldehyde was used as the test contaminant at 2 ppm(v/v). The test cell was irradiated from above with a 365 nm UV source at 7.0 $mW/cm^2$. The single pass conversion of formaldehyde was measured as a function of sphere depth.

The results of this experiment are summarized in Table 1. These results show that as more layers of spheres were added, increasing the bed depth, the single pass conversion of formaldehyde increased. Since the illumination of each successive coating decreases, the overall system volumetric performance decreases with increased bed depth as illustrated by the $k_{eff}a/V$ (space velocity normalized for conversion) metric.

$$\frac{K_{eff}a}{V} = \ln\left(\frac{C}{C_o}\right)\frac{F}{V} \quad (3)$$

where:
$K_{eff}$=effective rate constant
a=specific area
C, $C_o$=contaminant concentration at outlet and inlet of reactor, specifically
F=flow rate
V=reactor volume
However, the quantum efficiency improves with bed depth as the same light converts more contaminant. Also, $k_{eff}a/V$ does not decrease linearly with bed depth due to the increased efficiency associated with n<1 order of the reaction rate in light intensity as discussed earlier. Thus, increasing the bed depth for a given light input allows for some combination of greater fluid throughput or greater conversion. These results agree well with what would be predicted based on an analysis as described in Example 2.

TABLE 1

| Bed Depth, # Spheres | Formaldehyde Single Pass Conversion, % | $K_{eff}a/V$, $min^{-1}$ |
| --- | --- | --- |
| 1 | 58 | 305 |
| 2 | 74 | 230 |
| 3 | 85 | 219 |
| 4 | 90 | 197 |

Example 4

A reactor of the configuration depicted by FIG. 2 was simulated using computer models for reaction kinetics, mass transfer, irradiance distribution, and fluid mechanics. Such simulations are routinely used by the chemical process industry to evaluate potential reactor designs. Formaldehyde conversion in air, for a simulated reactor using brookite and anatase $TiO_2$ plus $ZrO_2$ coated soda-lime spheres as the packing, was calculated. The reaction kinetics parameters were determined by experiment. The transparency of the coating used to generate the kinetic data was 81% at 365 nm. A Voltarc Technologies F18T8/BL9/HO/BP lamp was modeled based on emission measurements. A formaldehyde concentration of 2 ppm and a relative humidity of 40% were used. The dimensions of the face of the reactor were 61×46 cm. The lamps were spaced evenly throughout the reactor. The lamp sleeve diameter was 2.6 cm. The effect on single pass formaldehyde conversion and pressure drop of variations in flow rate, number of lamps, sphere diameter for fixed number depth, and packing depth for a fixed sphere diameter were determined.

Table 2 shows the effect of increasing airflow through the reactor on performance. Increased throughput results in decreased single pass conversion and higher pressure drop. However, due to improved mass transfer at higher flow rates, the decrease is less than would be expected based on decreased residence time alone. The $k_{eff}a/V$ metric, which normalizes the performance of the system for flow and volume differences, shows the increase in relative performance as the flow rate is increased. The operating flow rate for a given reactor will be determined by weighing the pressure drop and performance along with other considerations such as noise.

TABLE 2

| Reactor Depth, cm | Packing Sphere Diameter, cm | Air Flow Rate, $m^3$/min | Number of lamps | Single Pass Conversion, % | $K_{eff}a/V$, $min^{-1}$ | ΔP, in WC |
| --- | --- | --- | --- | --- | --- | --- |
| 5.5 | 0.3 | 1.4 | 6 | 96 | 292 | 0.15 |
|  |  | 2.8 |  | 85 | 345 | 0.4 |
|  |  | 4.2 |  | 74 | 367 | 0.7 |
|  |  | 5.7 |  | 64 | 378 | 1.1 |

Table 3 shows the effect of decreasing the number of lamps on single pass conversion. For the given packing size and reactor dimension adding lamps up to eight results in a nearly linear improvement in normalized performance (as described by $k_{eff}a/V$.) The light from each lamp penetrates throughout the reactor and so increases the reaction rate everywhere in the bed, not just near to the lamp sleeve. There is a small, but insignificant, change in pressure drop as the number of lamps is increased due to the lamps taking up volume, and thus decreasing active reactor volume and increasing the velocity of the gas through the bed. The number of lamps actually used in a reactor will be determined by comparing lamp and ballast cost against increased performance.

TABLE 3

| Reactor Depth, cm | Packing Sphere Diameter, cm | Air Flow Rate, Nm³/min | Number of lamps | Single Pass Conversion, % | $K_{eff}a/V$, min⁻¹ | ΔP, in WC |
|---|---|---|---|---|---|---|
| 5.5 | 0.3 | 2.83 | 8 | 92 | 551 | 0.4 |
|  |  |  | 7 | 90 | 475 |  |
|  |  |  | 6 | 85 | 383 |  |
|  |  |  | 5 | 77 | 290 |  |
|  |  |  | 4 | 65 | 205 |  |
|  |  |  | 3 | 50 | 133 |  |

Table 4 shows the effect of increasing the diameter of the spherical packing material for a reactor with a fixed packing number depth. For this case the larger packing size and increased bed depth balance to produce little change in absolute formaldehyde removal, but the normalized performance decreases because of the larger reactor size needed to accomplish the same result. Pressure drop decreases as the packing size is increased even though the bed is thicker. The choice of packing diameter in a reactor will consider the tradeoff between pressure drop and the size (and importantly weight) of the reactor.

TABLE 4

| Reactor Depth, cm | Packing Sphere Diameter, cm | Air Flow Rate, Nm³/min | Number of lamps | Single Pass Conversion, % | $K_{eff}a/V$, min⁻¹ | ΔP, in WC |
|---|---|---|---|---|---|---|
| 5.5 | 0.3 | 2.83 | 6 | 85 | 383 | 0.4 |
| 6.5 | 0.4 |  |  | 86 | 341 | 0.3 |
| 7.5 | 0.5 |  |  | 87 | 302 | 0.25 |
| 8.5 | 0.6 |  |  | 87 | 231 | 0.2 |

Table 5 shows the effect of increasing the reactor depth dimension with a fixed packing size. Here a tradeoff between absolute performance increase and normalized performance is observed. For a given number of lamps the marginal increase in performance decreases as the reactor is made larger and the pressure drop is increased.

TABLE 5

| Reactor Depth, cm | Packing Sphere Diameter, cm | Air Flow Rate, Nm³/min | Number of lamps | Single Pass Conversion, % | $K_{eff}a/V$, min⁻¹ | ΔP, in WC |
|---|---|---|---|---|---|---|
| 3.7 | 0.3 | 2.83 | 6 | 75 | 416 | 0.27 |
| 5.5 |  |  |  | 85 | 383 | 0.40 |
| 6.7 |  |  |  | 88 | 351 | 0.49 |
| 7.9 |  |  |  | 89 | 310 | 0.57 |

The examples above are typical of conceptual design studies that are done to find the best use of the current invention for a given situation. The examples illustrate the appraisal of design variables in designing a photocatalytic reactor.

Example 5

Oxidation of acetone in ultra-pure water was examined in a small laboratory system. Ultra-pure water (>17 MΩ-cm) was charged with 40 ppb acetone and passed through a bed of irradiated photocatalyst coated 6 mm glass spheres. The dissolved oxygen of the water was 8.6 ppm. The bed was 4.5 cm in diameter, 3 cm deep, and illuminated from above with 365 nm ultraviolet radiation. The coating on the substrate allowed 80% transmission of the 365 nm light. The UV flux at the top of the bed was 10 mW/cm². The measured $k_{eff}a/V$ for acetone oxidation under these conditions was 0.6 min⁻¹.

Spheres are a less effective substrate configuration compared to various other packing materials because they have a lower specific surface area and a low bed void fraction as much of the bed is inert glass. For example, a smaller diameter, higher efficiency, support material such as 4 mm Berl saddles would provide a $k_{eff}a/V>2$ min⁻¹. Despite the lower efficiency, the 6 mm spheres gave a useful performance for acetone removal in applications where low concentrations of organic material need to be removed from water, such as purification of semiconductor rinse water.

We claim:

1. An apparatus for photocatalytic conversion of contaminants in a fluid stream, said apparatus comprising:
    a reactor enclosure having a fluid inlet and a fluid outlet;
    at least one semiconductor unit in fluid communication with said fluid inlet and said fluid outlet, said semiconductor unit including a transparent or semi-transparent, three-dimensional substrate having a semi-transparent semiconductor photocatalytic surface with which the fluid stream comes into contact; and
    a light emitting device in optical proximity and communication to said at least one semiconductor unit, said light emitting device providing incident light having a wavelength corresponding to a semitransparent region of the absorption spectrum of the semiconductor unit;
    wherein said photocatalytic surface is of sufficient thickness to pass 60–95% of the incident light directed to said surface; said substrate is of sufficient thickness to pass greater than 80% of the incident light directed to said substrate; and said light emitting device and said semiconductor unit work cooperatively to remove contaminants in the fluid stream by photocatalytic reaction, said reaction having a reaction order, in respect to light intensity, that is less than unity.

2. The apparatus of claim 1, wherein said at least one semiconductor unit has multiple photocatalytic surfaces and is configured to permit the light to pass through said multiple surfaces.

3. The apparatus of claim 1, wherein said photocatalytic surface and said substrate comprise the same material.

4. The apparatus of claim 1, wherein a photocatalytic material is incorporated into the substrate.

5. The apparatus of claim 1, wherein said semiconductor unit comprises a layer of semitransparent material bonded to said substrate.

6. The apparatus of any one of claims 3, 4 or 5, wherein said photocatalytic surface of claim 3, said photocatalytic material of claim 4 or said semitransparent material of claim 5 includes at least one co-catalyst.

7. The apparatus of claim 6, wherein said at least one co-catalyst material is selected from the group consisting of platinum, palladium, ruthenium, iridium, rhodium, gold, silver, copper, tin, iron, cobalt, vanadium, niobium, zirconium and zinc or their oxides or sulfides.

8. The apparatus of claim 1, wherein said photocatalytic surface is 0.1–1 $\mu$m thick.

9. The apparatus of claim 1, wherein said photocatalytic surface is selected from the group consisting of $TiO_2$, $ZrO_2$, ZnO, $CaTiO_3$, $SnO_2$, $MoO_3$, $Fe_2O_3$, and $WO_3$.

10. The apparatus of claim 1, wherein said photocatalytic surface contains one or more of the polymorphs of $TiO_2$.

11. The apparatus of claim 1 or claim 10, wherein said at least one semiconductor unit is partially transparent to incident light having a wavelength between 340 and 390 nm.

12. The apparatus of claim 1, wherein said substrate is a semitransparent, open-cell, three dimensionally reticulated, and fluid permeable structure.

13. The apparatus of claim 12, wherein said at least one semiconductor unit has a pore size ranging from about 10 to about 200 pores per square inch.

14. The apparatus of claim 1, wherein said substrate is packing material selected from the group consisting of spheres, cylinders, raschig rings, pall rings, lessing rings, partition rings, berl saddles, intalox saddles, and tellerettes with characteristic length >0.1 cm.

15. The apparatus of claim 1, wherein said substrate comprises a material or materials selected from the group consisting of alumina, zirconia, titania, silica, fused silica, glass, silicone, and organic polymers.

16. The apparatus of claim 1 or claim 15, wherein said substrate comprises an organic polymer that is resistant to yellowing when exposed to said incident light.

17. The apparatus of claim 1, wherein said light emitting device is selected from the group consisting of light emitting diode, low pressure mercury lamp, medium pressure mercury lamp, high pressure mercury lamp, xenon lamp, and the sun.

18. The apparatus of claim 1, wherein said reaction order is about one-half.

19. A method for photocatalytic conversion of contaminants in a fluid stream, comprising:

providing a reactor enclosure having a fluid inlet and a fluid outlet;

providing at least one semiconductor unit in fluid communication with said fluid inlet and said fluid outlet, said semiconductor unit including a transparent or semi-transparent, three-dimensional substrate having a semi-transparent semiconductor photocatalytic surface with which the fluid stream comes into contact;

providing a light emitting device in optical proximity and communication to said at least one semiconductor unit;

directing incident light having a wavelength corresponding to a semitransparent region of the absorption spectrum of the semiconductor unit toward said semiconductor unit, wherein the photocatalytic surface is of sufficient thickness to pass 60–95% of the incident light directed to the surface and the substrate is of sufficient thickness to pass greater than 80% of the incident light directed to the substrate; and converting contaminants in the fluid stream by photocatalytic reaction, the reaction having a reaction order, in respect to light intensity, that is less than unity.

20. The method of claim 19, wherein said at least one semiconductor unit has multiple photocatalytic surfaces and further comprising directing the light to pass through the multiple surfaces.

21. The method of claim 19, wherein said photocatalytic surface and said substrate comprise the same material.

22. The method of claim 19, wherein a photocatalytic material is incorporated into the substrate.

23. The method of claim 19, wherein said semiconductor unit comprises a layer of semitransparent material bonded to said substrate.

24. The method of any one of claims 21, 22, or 23, wherein said photocatalytic surface of claim 21, said photocatalytic material of claim 22 or said semitransparent material of claim 23 includes at least one co-catalyst.

25. The method of claim 24, wherein said at least one co-catalyst material is selected from the group consisting of platinum, palladium, ruthenium, iridium, rhodium, gold, silver, copper, tin, iron, cobalt, vanadium, niobium, zirconium and zinc or their oxides or sulfides.

26. The method of claim 19, wherein said photocatalytic surface is 0.1–1 $\mu$m thick.

27. The method of claim 19, wherein said photocatalytic surface is selected from the group consisting of $TiO_2$, $ZrO_2$, ZnO, $CaTiO_3$, $SnO_2$, $MoO_3$, $Fe_2O_3$, and $WO_3$.

28. The method of claim 19, wherein said photocatalytic surface contains one or more of the polymorphs of $TiO_2$.

29. The method of claim 19 or claim 28, wherein at least one semiconductor unit is partially transparent to incident light having a wavelength between 340 and 390 nm.

30. The method of claim 19, wherein said substrate is a semitransparent, open-cell, three dimensionally reticulated, and fluid permeable structure.

31. The method of claim 29, wherein said at least one semiconductor unit has a pore size ranging from about 10 to about 200 pores per square inch.

32. The method of claim 19, wherein said substrate is packing material selected from the group consisting of spheres, cylinders, raschig rings, pall rings, lessing rings, partition rings, berl saddles, intalox saddles, and tellerettes with characteristic length >0.1 cm.

33. The method of claim 19, wherein said substrate comprises a material selected from the group consisting of alumina, zirconium, titania, silica, fused silica, glass, silicone, and organic polymers.

34. The method of claim 19 or claim 33, wherein said substrate comprises an organic polymer that is resistant to yellowing when exposed to the incident light.

35. The method of claim 19, wherein said light emitting device is selected from the group consisting of light emitting diode, low pressure mercury lamp, medium pressure mercury lamp, high pressure mercury lamp, xenon lamp, and the sun.

36. The method of claim 19, wherein the reaction order is about one-half.

* * * * *